United States Patent
McNicholas

(10) Patent No.: US 10,470,464 B2
(45) Date of Patent: Nov. 12, 2019

(54) DEER LURE COMPOSITION AND METHOD OF USE IN CONDUCTING A CENSUS OF LOCAL DEER POPULATION

(71) Applicant: John Walter McNicholas, New Cumberland, WV (US)

(72) Inventor: John Walter McNicholas, New Cumberland, WV (US)

( * ) Notice: Subject to any disclaimer, the term of this patent is extended or adjusted under 35 U.S.C. 154(b) by 0 days.

(21) Appl. No.: 15/990,597

(22) Filed: May 26, 2018

(65) Prior Publication Data

US 2018/0271104 A1    Sep. 27, 2018

Related U.S. Application Data

(62) Division of application No. 13/592,310, filed on Aug. 22, 2012, now Pat. No. 9,980,492.

(60) Provisional application No. 61/535,879, filed on Sep. 16, 2011.

(51) Int. Cl.
| | |
|---|---|
| *A01N 63/02* | (2006.01) |
| *A01N 25/22* | (2006.01) |
| *A01N 25/02* | (2006.01) |
| *A61K 35/55* | (2015.01) |
| *A61K 9/107* | (2006.01) |
| *A01M 31/00* | (2006.01) |

(52) U.S. Cl.
CPC .......... *A01N 63/02* (2013.01); *A01M 31/002* (2013.01); *A01N 25/02* (2013.01); *A01N 25/22* (2013.01); *A61K 9/107* (2013.01); *A61K 35/55* (2013.01); *A01N 2300/00* (2013.01)

(58) Field of Classification Search
CPC ........ A01N 63/02; A01N 25/02; A01N 25/22; A01N 2300/00; A61K 35/55; A61K 9/107; A01M 31/002
See application file for complete search history.

(56) References Cited

U.S. PATENT DOCUMENTS

| | | | | |
|---|---|---|---|---|
| 4,944,940 A | * | 7/1990 | Christenson, II | ...... A01N 63/02 424/84 |
| 2012/0282315 A1 | * | 11/2012 | Tate | ...... A01N 63/02 424/409 |

OTHER PUBLICATIONS

West Virginia Scent Maker Carves a Niche, Oct. 7, 2009, MetroNews in Outdoors.*
Backwoods Bound Bulletin Board, Dec. 4, 2007, how to make a homemade deer attractant or lure.*
Backwood Bound Bulletin Board, How to make a homemade deer attractant or lure, Dec. 4, 2007.
Forum posted to TradeGang.com, topic: Smokey's Pre-Orbital Results after only eight days posted Sep. 18, 2010.
West Virginia Scent maker Carves a Niche, Oct. 7, 2009, WV MetroNews.

* cited by examiner

*Primary Examiner* — John Pak
*Assistant Examiner* — Nathan W Schlientz
(74) *Attorney, Agent, or Firm* — Price & Adams, P.C.

(57) ABSTRACT

A deer lure is applied to a licking branch to attract deer, primarily buck deer, in collecting census data on the population of a deer herd in a given area and in deer hunting. The lure is formulated by surgically removing the left and right pre-orbital tear duct glands from the left and right eyes of a deer. The left and right pre-orbital tear duct glands are mixed together to produce a totally pure pre-orbital gland lure, free of any other product removed from any deer. When applied to a licking branch, the lure is effective in attracting deer year round to the licking branch and is not limited to use during the rut.

13 Claims, 1 Drawing Sheet

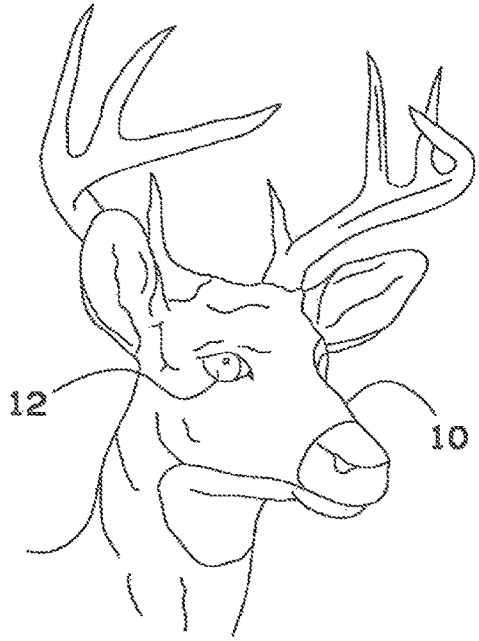

FIG.1

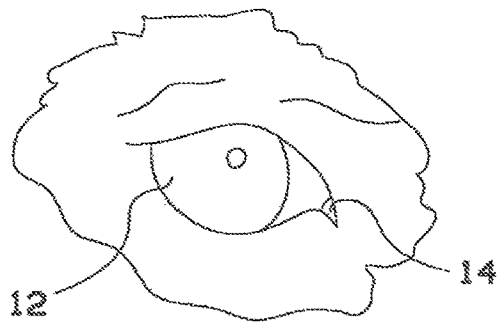

FIG.2

```
┌─────────────────────────────────────┐
│ TO PRODUCE A TOTALLY PURE PRE-ORBITAL│
│ GLAND LURE IT IS CRUCIAL THAT THE   │
│ RIGHT AND LEFT PRE-ORBITAL TEAR     │
│ DUCT GLANDS ARE SURGICALLY REMOVED  │
│ FROM SPECIFIC SPECIES OF DEER FOR   │
│ WHICH THE LURE IS BEING CREATED.    │
└─────────────────────────────────────┘
                  │
                  ▼
┌─────────────────────────────────────┐
│ THE GLANDS ARE THEN MATCHED         │
│ TOGETHER TO DO A TOTAL DNA OF       │
│ THAT SPECIFIC FAMILY OF DEER        │
└─────────────────────────────────────┘
                  │
                  ▼
┌─────────────────────────────────────┐
│ THE DNA SOLUTION IS USED TO         │
│ SOAK GLANDS TOGETHER: EMULSIFY IN   │
│ GLYCERIN, PROPYLENE GLYCOL, OR IN   │
│ 90 TO 193 PROOF ALCOHOL SUCH AS     │
│ VODKA OR ANY OTHER PROOF ALCOHOL    │
└─────────────────────────────────────┘
                  │
                  ▼
┌─────────────────────────────────────┐
│ A FIXATIVE, SUCH AS SMALL AMOUNTS   │
│ OF TONQUIN MUSK, REAL OR IMITATION, │
│ AND OR SIBERIAN MUSK ARE THEN ADDED │
│ TO COMPLETE THE PRODUCT             │
└─────────────────────────────────────┘
```

FIG.3

DEER LURE COMPOSITION AND METHOD OF USE IN CONDUCTING A CENSUS OF LOCAL DEER POPULATION

CROSS-REFERENCE TO RELATED APPLICATION

This application is a division of U.S. application Ser. No 13/592,310 "Lure Useful to Obtain Census on Local Buck Deer and in Deer Hunting" filed on Aug. 22, 2012 which claims the benefit of priority of U.S. provisional application No. 61/535,879, filed Sep. 16, 2011, the contents of which are herein incorporated by reference.

BACKGROUND OF THE INVENTION

The present invention relates to deer lures and, more particularly, to a lure to be used to obtain census on local buck deer and in deer hunting.

Deer hunters and photographers often have a problem with collecting data on deer herds in specific locations. Creating an inventory of deer available to hunt or photograph using trail cameras has proven difficult.

Recent research has shown that the licking branch is the number one key to success when hunting a mock scrape. Bucks secrete a scent as a means of distinctly identifying themselves from the competition, helping them to understand their rank in the pecking order among the bucks in a given area. Bucks can keep tabs on one another by using licking branches and they do this year round. Bucks regularly visit licking branches and become aware when a new rival shows up when the licking branch has a scent of an unrecognized buck.

As can be seen, there is a need for a method and lure for obtaining census on local buck deer and in deer hunting, solving the problems that deer hunters and photographers had in the past of collecting data on their herds in specific locations.

SUMMARY OF THE INVENTION

In accordance with the present invention there is provided a composition for a deer lure consisting essentially of a mixture made by removing from a deer a left pre-orbital tear duct gland from the left eye and a right pre-orbital tear duct gland from the right eye of the same deer. The mixture contains no other deer based product. The tear duct glands are soaked together in a solution selected from the group consisting of glycerin, propylene glycol, and alcohol in the range of 90 to 193 proof to provide the mixture made purely of the duct glands and the solution.

Further in accordance with the present invention there is provided a method for conducting a census of the deer population in a given area that includes the steps of applying to a licking branch used to attract deer a composition comprising a mixture of the left and right pre-orbital tear duct glands removed from a deer and no other deer product, and a solution formed of glycerin, propylene glycol, or alcohol in the range of 90 to 193 proof. An image is obtained of a deer attracted to the licking branch in response to the composition. Census data is collected from the deer attracted to the licking branch for the purpose of creating a census of the deer population in the given area.

These and other features, aspects and advantages of the present invention will become better understood with reference to the following drawings, description and claims.

BRIEF DESCRIPTION OF THE DRAWINGS

FIG. 1 is a perspective view of a head of a deer;
FIG. 2 is a detailed perspective view showing a pre-orbital tear duct gland of a deer; and
FIG. 3 is a flow diagram, illustrating a method for producing a lure according to an exemplary embodiment of the present invention.

DETAILED DESCRIPTION OF THE INVENTION

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Broadly, an embodiment of the present invention provides a deer lure and a method for making a deer lure. The lure allows hunters and photographers to easily attract deer, primarily bucks, in specific locations for the purpose of collecting census data on the bucks. The lure is a pre-orbital gland lure where left and right pre-orbital glands are matched together to provide a total DNA of that specific family of deer.

Referring now to FIGS. 1 and 2, a pre-orbital gland 14 from both the left and right eyes 12 of a deer 10 are used to produce the lure. By using both left and right pre-orbital glands matched together, a total DNA of that specific family of deer.

Referring now to FIG. 3, to produce a totally pure pre-orbital gland lure, both the left and right pre-orbital tear duct glands are surgically removed from the deer, the species being the same as that for which the lure is being created. The glands are then matched together to provide a total DNA of that specific family of deer. The glands can be soaked together in a DNA solution, emulsified in glycerin, propylene glycol, or in 90 to 193 proof alcohol, such as vodka or other proof alcohol. A fixative, such as small amounts of Tonquin Musk, real or imitation, and/or Siberian Musk, can be added.

The lure can be used, for example, beginning in July through October, to learn the big and small buck inventory in a particular hunting location. The lure can be used throughout the season, especially in the rut. An existing licking branch from a prior season or a new mock licking branch can be used to attract all the bucks in a given area. By applying a small amount directly to the branch, each buck will be curious about the new buck who is invading his territory. The lure can be reapplied as needed, typically on each visit to the location.

It should be understood, of course, that the foregoing relates to exemplary embodiments of the invention and that modifications may be made without departing from the spirit and scope of the invention as set forth in the following claims.

I claim:

1. A composition for a deer lure consisting essentially of:
a mixture made by removing from a deer a left pre-orbital tear duct gland from the left eye and a right pre-orbital tear duct gland from the right eye of the same deer, wherein the mixture contains no other deer based product; and soaking the tear duct glands together in a solution selected from the group consisting of glycerin, propylene glycol, and alcohol in the range of 90 to 193 proof, to provide said mixture which is made purely of said tear duct glands and said solution;

wherein the composition does not contain any other deer based product.

2. A method for conducting a census of the deer population in a given area comprising the steps of,
applying to a licking branch used to attract deer a composition according to claim 1
obtaining an image of deer attracted to the licking branch in response to said composition applied to the licking branch, and
collecting census data from the deer attracted to the licking branch to create an inventory of the deer population in the given area.

3. The method as set forth in claim 2 which includes,
collecting data on each visit the deer make to the licking branch to create an inventory of deer populated in the given area for hunting the deer.

4. The method as set forth in claim 2 which includes,
identifying the buck deer in the inventory of the deer population created from the census data.

5. The method as set forth in claim 2 which includes,
creating the inventory of the deer population in the given area by obtaining an image of the deer attracted to the licking branch.

6. The method as set forth in claim 2 which includes,
identifying from the inventory of the deer population created by the census data the number of big and small buck deer in the deer population in the given area.

7. The method as set forth in claim 2 which includes,
using a trail camera to record each visit of the deer attracted to the licking branch for the purpose of identifying the buck deer in the given area.

8. The method as set forth in claim 2 which includes,
observing each visit of deer attracted to the licking branch for a selected period of time during the calendar year to obtain an inventory of large and small buck deer in the given area for the selected period of time.

9. The method as set forth in claim 8 which includes,
observing each visit of deer attracted to the licking branch for the period of time in a calendar year July through October.

10. The method as set forth in claim 8 which includes,
observing each visit of deer attracted to the licking branch for the period of time during the rut season.

11. The method as set forth in claim 8 which includes,
repeatedly applying said composition to the licking branch throughout the calendar year.

12. The method as set forth in claim 2 which includes,
observing the licking branch to detect the visits of deer attracted to the licking branch on a periodic basis, and
reapplying said composition to the licking branch after each visit by the deer.

13. The method as set forth in claim 2 which includes,
applying said composition to a mock licking branch used to attract buck deer to the given area.

* * * * *